United States Patent [19]

Green et al.

[11] Patent Number: 5,257,713

[45] Date of Patent: * Nov. 2, 1993

[54] SURGICAL FASTENING DEVICE

[75] Inventors: David T. Green, Westport; Henry Bolanos, East Norwalk; Dominick L. Mastri, Bridgeport; Richard A. McGarry, Norwalk, all of Conn.; Wayne P. Young, Brewster, N.Y.

[73] Assignee: United States Surgical Corporation, Norwalk, Conn.

[ * ] Notice: The portion of the term of this patent subsequent to Jun. 8, 2010 has been disclaimed.

[21] Appl. No.: 931,591

[22] Filed: Aug. 18, 1992

Related U.S. Application Data

[63] Continuation-in-part of Ser. No. 696,511, May 7, 1991.

[51] Int. Cl.$^5$ ............................................. A61B 17/00
[52] U.S. Cl. ..................................................... 227/19
[58] Field of Search .................. 606/143, 219; 227/19, 227/175, 178, 179, 180

[56] References Cited

U.S. PATENT DOCUMENTS

| Re. 28,932 | 8/1976 | Noiles et al. | |
|---|---|---|---|
| 389,660 | 9/1888 | Mandel et al. | 606/220 |
| 3,054,406 | 9/1962 | Usher | 606/152 |
| 3,124,136 | 3/1964 | Usher | 606/152 |
| 3,494,533 | 2/1970 | Green et al. | |
| 3,643,851 | 2/1972 | Green et al. | |
| 3,837,555 | 9/1974 | Green | |
| 4,014,492 | 3/1977 | Rothfuss | 227/19 |
| 4,027,510 | 6/1977 | Hiltebrandt | 72/37 |
| 4,043,504 | 8/1977 | Hueil et al. | 227/19 |
| 4,127,227 | 11/1978 | Green | |
| 4,196,836 | 4/1980 | Becht | 227/110 |
| 4,204,623 | 5/1980 | Green | 227/19 |
| 4,256,251 | 3/1981 | Moshofsky | 227/19 |
| 4,261,244 | 4/1981 | Becht et al. | 411/472 |
| 4,347,847 | 9/1982 | Usher | 606/152 |
| 4,349,028 | 9/1982 | Green | 227/19 |
| 4,375,866 | 3/1983 | Giersch et al. | 227/19 |
| 4,403,693 | 9/1983 | Froehlich | 411/457 |
| 4,407,286 | 10/1983 | Noiles | 227/19 |
| 4,452,245 | 6/1984 | Usher | 606/152 |
| 4,489,875 | 12/1984 | Crawford et al. | 227/19 |
| 4,496,090 | 1/1985 | Crevier et al. | 227/19 |
| 4,505,273 | 3/1985 | Braun et al. | 606/219 |
| 4,509,518 | 4/1985 | McGarry et al. | |
| 4,520,817 | 6/1985 | Green | |
| 4,523,695 | 6/1985 | Braun et al. | 227/19 |
| 4,523,707 | 6/1985 | Blake, III et al. | 227/19 |
| 4,526,174 | 7/1985 | Froehlich | 606/219 |

(List continued on next page.)

FOREIGN PATENT DOCUMENTS

| 0061867 | 4/1982 | European Pat. Off. | |
|---|---|---|---|
| 0174843 | 9/1986 | European Pat. Off. | |
| 0354724 | 3/1990 | European Pat. Off. | |
| 2330182 | 1/1975 | Fed. Rep. of Germany | |
| 2703529 | 8/1978 | Fed. Rep. of Germany | 609/219 |
| 1234670 | 5/1960 | France | |
| 8505025 | 7/1985 | PCT Int'l Appl. | |
| 2233903 | 11/1991 | United Kingdom | |

OTHER PUBLICATIONS

Information Booklet for Auto Suture® Multifire Premium ™ Disposable Skin Stapler and Disposable Loading Unit.
Information Booklet for Auto Suture® Skin & Fascia Suture® Surgical Stapling Instruments.

Primary Examiner—Stephen C. Pellegrino
Assistant Examiner—Gary Jackson

[57] ABSTRACT

A surgical instrument for placing fasteners and/or a reinforcement material in tissue is provided. Structure is provided for advancing the fasteners distally by an actuating handle means working in concert with a pusher means. The fasteners exit the fastener housing at an angle to the longitudinal axis of the device to facilitate visualization and placement at the surgical site. A unique fastener may be formed in which the legs are in a substantially overlapping longitudinally-spaced relation.

12 Claims, 8 Drawing Sheets

U.S. PATENT DOCUMENTS

| | | | |
|---|---|---|---|
| 4,532,927 | 8/1985 | Miksza, Jr. | 606/220 |
| 4,566,620 | 1/1986 | Green et al. | |
| 4,583,670 | 4/1986 | Alvarado | 227/19 |
| 4,607,638 | 8/1986 | Crainich | 411/472 |
| 4,610,251 | 9/1986 | Kumar | 411/460 |
| 4,616,650 | 10/1986 | Green et al. | |
| 4,618,086 | 10/1986 | Li et al. | 227/19 |
| 4,624,254 | 11/1986 | McGarry et al. | |
| 4,634,035 | 1/1987 | Li et al. | 227/19 |
| 4,655,221 | 4/1987 | Devereux | 606/152 |
| 4,662,555 | 5/1987 | Thornton | 227/219 |
| 4,664,305 | 5/1987 | Blake, III et al. | |
| 4,719,917 | 1/1988 | Barrows et al. | 606/219 |
| 4,728,020 | 3/1988 | Green et al. | |
| 4,747,531 | 5/1988 | Brinkerhoff et al. | 227/19 |
| 4,787,387 | 11/1988 | Burbank, III et al. | 227/19 |
| 4,802,478 | 2/1989 | Powell | |
| 4,807,628 | 2/1989 | Peters et al. | 227/19 |
| 4,821,942 | 4/1989 | Richards et al. | 227/19 |
| 4,899,745 | 2/1990 | Laboureau et al. | 606/142 |
| 4,919,152 | 4/1990 | Ger | 128/898 |
| 4,919,320 | 4/1990 | Storace | 227/19 |
| 4,934,364 | 6/1990 | Green | |
| 4,944,443 | 7/1990 | Oddsen et al. | 227/19 |
| 4,978,049 | 12/1990 | Green | 227/178 |
| 5,040,715 | 8/1991 | Green et al. | 227/180 |
| 5,100,420 | 3/1992 | Green et al. | 606/143 |
| 5,125,553 | 6/1992 | Oddsen et al. | 227/175 |

FIG. I

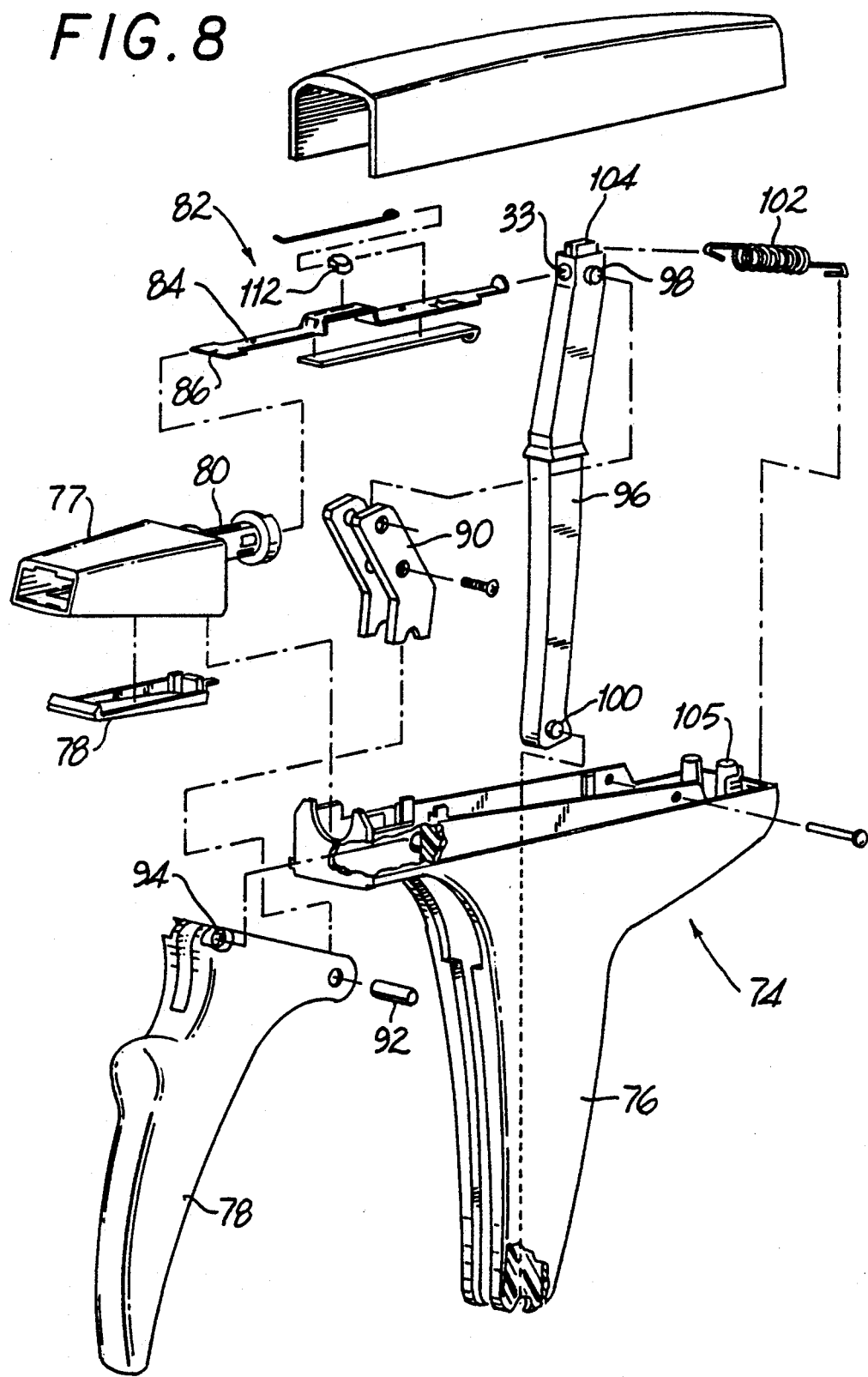

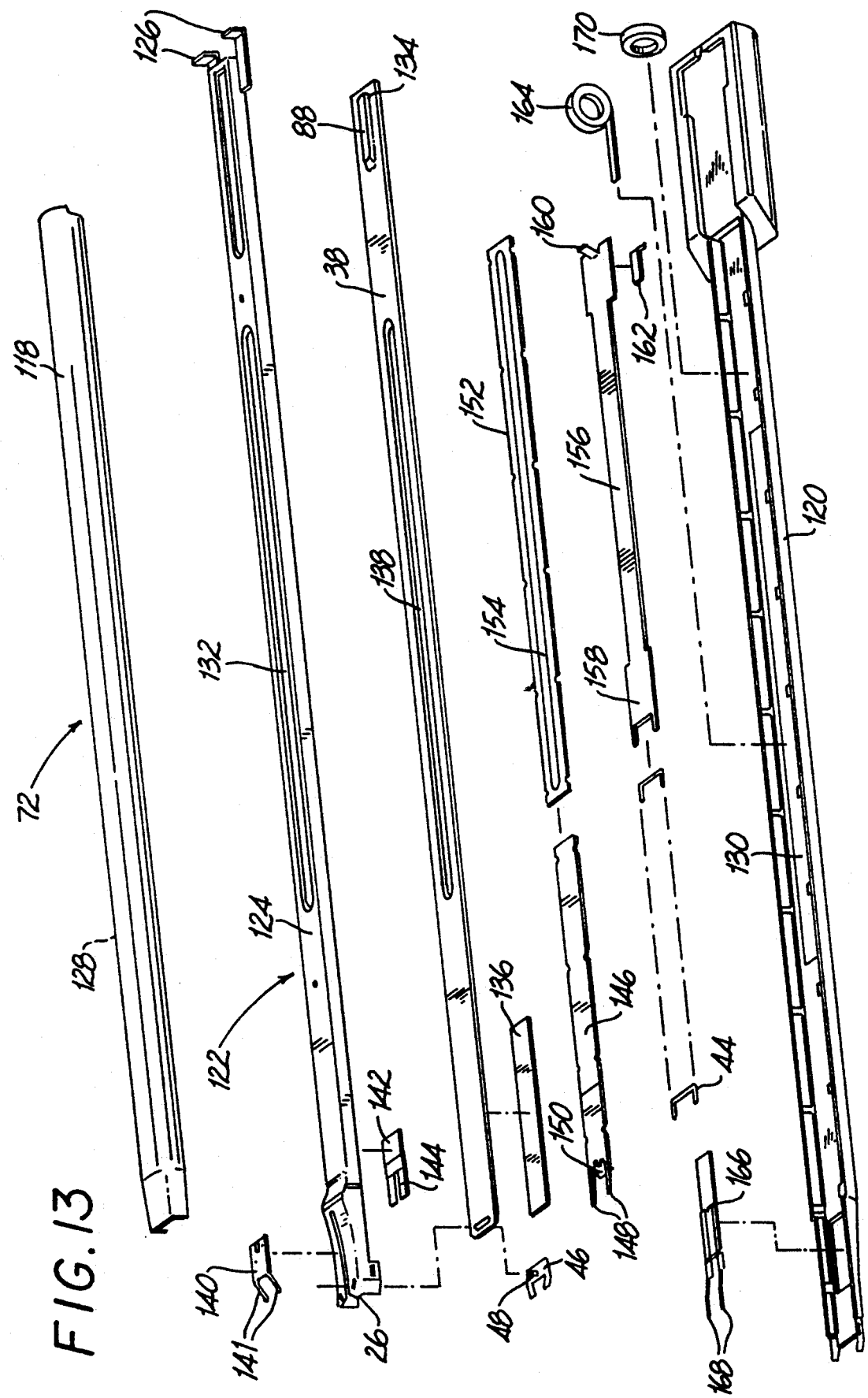

SURGICAL FASTENING DEVICE

CROSS REFERENCE TO RELATED APPLICATION

This application is a continuation-in-part of commonly assigned, copending U.S. patent application Ser. No. 07/696,511, filed May 7, 1991.

BACKGROUND OF THE INVENTION

1. Technical Field

The present invention relates to a device for applying clips or staples to tissue, and more particularly to a unique delivery system adapted for endoscopic application of clips/staples. The system is useful for repairing defects in the body wall, e.g., by securing a mesh to the wall in the region of the defect.

2. Background of the Invention

The placement of clips and staples in surgical procedures is well known. For example, U.S. Pat. Nos. 4,616,650 to Green et al. and 4,934,364 to Green disclose clip appliers for placing clips, both absorbable and non-absorbable, on tissue and vessels. The clips are fed successively into the instrument jaws and cammed closed. Instruments for placing a plurality of staples on tissue and optionally cutting therebetween are disclosed in U.S. Pat. Nos. 3,494,533 to Green et al. and 4,520,817 to Green. The staples are supplied in pre-loaded cartridges and are formed through contact with oppositely positioned anvil pockets.

An important consideration in the design and utilization of surgical clip appliers and staplers is the visibility and ease of instrument positioning provided to the surgeon. One approach has been to provide a stapler having a fastener applying assembly that articulates relative to the actuator assembly, as disclosed in U.S. Pat. Nos. 4,566,620 and 4,728,020 to Green et al. It has also been suggested to provide a surgical clip applier with a longitudinally curved sleeve, as disclosed in U.S. Pat. Nos. 4,509,518 and 4,624,254 to McGarry et al., and 4,664,305 to Blake.

Instruments for surgically stapling disunited skin of a patient to effect joining of the skin are also known. These instruments typically form substantially box-shaped staples by bending each staple around an anvil placed against the skin, and may be adapted to permit rotation of the staple forming assembly relative to the handles. See, e.g., U.S. Pat. Nos. 3,643,851 to Green et al. and Re. 28,932 to Noiles et al. Fascia staplers have also been disclosed which form fascia staples having a unique geometry for holding fascia tissue. See, e.g., U.S. Pat. No. 4,127,227 to Green.

More recently, attention has focused on minimally-invasive surgical procedures and instruments for facilitating such procedures. Minimally-invasive procedures are typically performed endoscopically through trocar sleeves or cannulas. Prior to introducing the cannula through the body wall, the surgeon generally insufflates the body cavity with carbon dioxide, e.g., through a Verres needle or like device. Insufflation creates a free area between internal body organs and the body wall. The surgeon then introduces one or more trocars through the body wall in to the insufflated body cavity to create a port of entry for accessory instrumentation. For example, graspers, dissectors, clip appliers, lasers and electrocautery devices are routinely employed endoscopically with the visual assistance of an endoscope and an external television monitor.

Endoscopic cholecystectomy (gall bladder removal) has recently met with tremendous clinical success and acceptance. Another procedure receiving attention for adaptation as a minimally-invasive surgical technique is hernia repair, with attention being primarily directly to all types of inguinal hernias (direct, indirect and femoral). A hernia involves the protrusion of an inner organ or body part through a defect in the muscle wall by which it is ordinarily contained. Historically, hernia repair has been performed by pulling the muscles together around the defect and suturing the muscles together, closing the hole but creating tension on the sutures. More recently, hernia defects have been repaired by suturing mesh over the defect. This approach patches the defect rather than drawing the spaced muscle walls together and/or ligating the hernia sac.

In order to facilitate surgical procedures, and particularly endoscopic procedures such as hernia repair, instrumentation is needed which provides the surgeon with improved visibility and which facilitates positioning of the instrument at the surgical site. A fastening system to provide optimal securement of a mesh or like device, preferably endoscopically, is also needed. These and other objectives are achieved by the present invention.

SUMMARY OF THE INVENTION

In accordance with the present invention, a surgical instrument for placing fasteners in or on tissue is provided which includes:

(a) a fastener housing having anvil means mounted at one end thereof and adapted to house at least one fastener therein;

(b) pusher means slidably received by said fastener housing, the pusher means comprising a pusher bar which defines a longitudinal axis and a pusher element slidably mounted to the pusher bar; and (c) slot means in the fastener housing, wherein the pusher means cooperates with the slot means to angularly displace the pusher element with respect to the longitudinal axis as the pusher means is advanced through the fastener housing.

The surgical instrument of the invention is thus adapted to angularly deliver a fastener to tissue with respect to the longitudinal axis of the instrument. Such angular delivery provides improved visibility to the surgeon and facilitates fastener placement in difficult tissue locations. The instrument is particularly suited for endoscopic applications, e.g., for securing a mesh to tissue in hernia repair.

In a preferred embodiment, the fastener housing contains a plurality of fasteners for sequential placement in tissue. Means are provided for advancing the fasteners distally and further means are provided for preventing more than one fastener from being placed in the "ready" position. A fastener may be placed by actuating handle means, e.g., a pistol handle, which effects distal movement of the pusher means. The fastener housing is preferably rotatable with respect to the handle means to further facilitate visibility and fastener placement.

According to the present invention, fasteners are angularly delivered to tissue through cooperation between slot means, pin means and cam means. The pusher element includes a contact face which is adapted to advance a fastener into engagement with and formation against the anvil means. The pusher element travels within a fastener track in the fastener housing, the width of which is only slightly larger than the width of the pusher element contact face. The pusher element is slidably mounted to the pusher bar by pin means extending through a transverse slot formed at the distal end of the pusher bar. Further slot means are formed in the fastener housing below the pusher bar. The pin means extends through the transverse slot to ride within the fastener housing slot means.

The fastener housing slot means causes the pusher element to jog as follows:

(i) the fastener housing slot means includes a first slot region which extends along the longitudinal axis of the instrument; the contact face of the pusher element is substantially perpendicular to the longitudinal axis of the instrument as the pin means travels within the first slot region;

(ii) distal to the first slot region, a second slot region communicates with and is angular oriented with respect to the first slot region; inasmuch as the pusher element is constrained in its transverse movement by the fastener track, as the pin means enters the second slot region the pin means moves within the transverse slot formed in the pusher bar and the pusher element rotates with respect to the pusher bar; and (iv) a third slot region communicates with the second and extends at an angle to the longitudinal axis of the instrument opposite to that of the second slot region; as the pin means enters the third slot region the pusher element is prevented from returning to its initial non-rotated orientation through contact with a cam face extending into the fastener track; thus, as the pin means moves back within the transverse slot, the pusher element retains its rotated position with respect to the pusher bar.

A unique fastener-forming assembly is also provided according to the present invention which includes:

(a) a fastener housing defining a fastener track having a center line and an opening at one end adapted to permit fastener exit;

(b) anvil means positioned adjacent the exit opening, the anvil means being positioned in a transverse and non-symmetrical orientation with respect to the center line; and (c) a fastener having a backspan and a pair of legs extending from the backspan at either end thereof; wherein contact of the fastener with the non-symmetrically positioned anvil causes the backspan of the fastener to bend such that the fastener legs assume a substantially over-lapping, longitudinally-spaced relation.

The fastener-forming assembly of the invention facilitates formation of a fastener particularly suited for securing an article, e.g., a reinforcement mesh, to tissue, as for example in hernia repair. The over-lapping configuration of the formed fastener allows the fastener legs to advance further than prior art fasteners prior to bending, thus facilitating fastener placement. Moreover, the substantially over-lapping, longitudinally-spaced orientation of the fastener legs provides excellent holding power when embedded in tissue. Preferably, the means for advancing the fastener into contact with the anvil means comprises a U-shaped pusher element having legs of differing widths so as to cooperate with the non-symmetrically positioned anvil means.

The instruments of the present invention are specifically suited for endoscopic applications. In such cases, the fastener formation system is typically fabricated as part of an endoscopic portion which is adapted for introduction through a trocar sleeve having a diameter of, for example, 10 to 15 mms. Internal sealing means are typically provided in the instrument, e.g., a sealing block, to ensure a gaseous seal when working in an insufflated body cavity.

BRIEF DESCRIPTION OF THE DRAWINGS

The accompanying figures referred to herein and constituting a part hereof illustrate preferred embodiments of the present invention, and together with the description, serve to explain the principles of the invention.

FIG. 8 is an exploded perspective view of a handle section of the endoscopic surgical instrument shown in FIG. 7;

FIG. 13 is an exploded perspective view illustrating the elongated endoscopic portion of the endoscopic surgical instrument shown in FIG. 7.

DETAILED DESCRIPTION OF THE INVENTION

A variety of actuation and fastener feeding mechanisms may be employed to advance the pusher means of the surgical instrument of the present invention to form and place fasteners. For example, the principles of the present invention may be adapted for use with a variety of handle configurations, e.g., pistol grips, scissor grips, palm grip, etc. Similarly, the fasteners of the invention may be stored and individually placed in the "ready" position using a variety of known mechanisms. Illustrative of such mechanisms are the pinion gear/pinion shaft mechanism and related structure disclosed in Re. 28,932 to Noiles et al., the belt mechanism and related structure disclosed in U.S. Pat. No. 3,837,555 to Green, and the mechanism and related structure of U.S. Pat. No. 4,204,623 to Green. The contents of these three commonly assigned U.S. patents are hereby incorporated by reference.

The present invention may be fabricated as a single, unitary assembly intended for single or multiple use, or practiced in association with a reusable actuating assembly which is adapted to receive a plurality of pre-loaded cartridges, whether in a single surgical procedure or, after sterilization, in further procedures. Such choices are well within the skill of one of ordinary skill in the art and are deemed to be within the scope of the present invention.

The following description shall be directed to fastener advancement and formation from the point at which a single fastener has been placed in the "ready" position, i.e., positioned adjacent pusher means adapted to advance the fastener into contact with the anvil means. As noted above, a variety of mechanisms and structure may be employed to position a fastener in the ready position.

Figure 1:
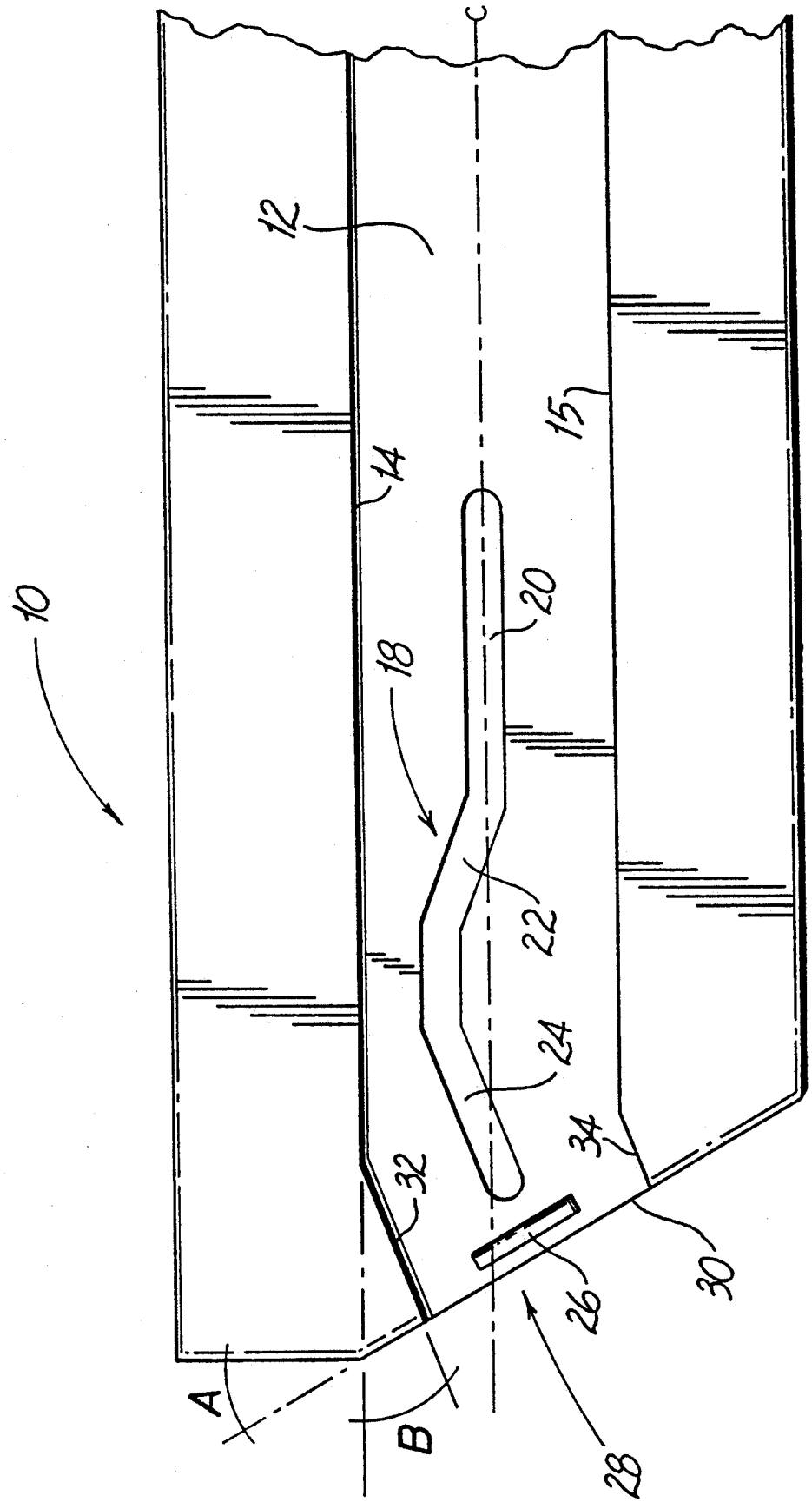
FIG. 1 is a schematic plan view of a distal portion of a fastener housing according to the present invention.

With reference to FIG. 1, a schematic plan view of the fastener housing in the region of fastener delivery is provided. Fastener housing 10 includes a fastener track 12 which extends substantially along the longitudinal axis of fastener housing 10. Fastener track 12 is defined by track walls 14, 15. Fastener track 12 is sized and dimensioned to receive an unformed fastener 44, as discussed hereinbelow.

A slot 18 is formed in fastener track 12 toward the distal end of fastener housing 10. Slot 18 comprises first slot region 20, second slot region 22 and third slot region 24. First slot region 20 extends substantially along the longitudinal axis of fastener housing 10 which is opposite to the angle of second slot region 22. Although, as illustrated, first and second slot regions 22, 24 are linear, a variety of geometries are possible, as for example arcuate slot paths.

An anvil 26 is positioned adjacent the outlet of fastener track 12. Anvil 26 is spaced from the termination of slot 18. Anvil 26 comprises a rigid material, e.g., stainless steel, which is sized and dimensioned to facilitate fastener formation therearound. Although FIG. 1 shows a single anvil 26 positioned in fastener track 12, additional anvil means are contemplated for incorporation into the instrument of the present invention, as for example the dual anvil sections (106,108) of U.S. Pat. No. 4,127,227 to Green, previously incorporated by reference.

The distal end 28 of fastener housing 10 includes an angled face 30 which is at an Angle A to the transverse axis of fastener housing 10. Angle A of angled face 30 is generally about 5° to 45° and preferably 15° to 25° relative to the transverse axis of fastener housing 10. Angle A may be less than 45° or greater than 5° by making appropriate adjustments to slot 18 and fastener track walls 14, 15, as discussed below.

Fastener track wall 14 forms an inwardly directed cam face 32 at its distal end. A corresponding, outwardly directed wall section 34 is formed at the distal end of track wall 15. By "inwardly" and "outwardly" directed is meant toward and away from the center line of fastener track 12, respectively. Cam face 32 and wall section 34 are preferably at an Angle B to the longitudinal axis of fastener housing 10. Angles A and B are preferably substantially equal.

Inwardly directed cam face 32 and outwardly directed wall section 34 cause fastener track 12 to angle with respect to the longitudinal axis of fastener housing 10. The width of fastener track 12 remains substantially constant throughout, i.e., in both its longitudinally oriented and angled regions. Third slot region 24 is typically at the same angle to the longitudinal axis as cam face 32 and wall section 34, i.e., Angle B. Anvil 26 is positioned transverse to the angled region of fastener track 12.

Figure 2:
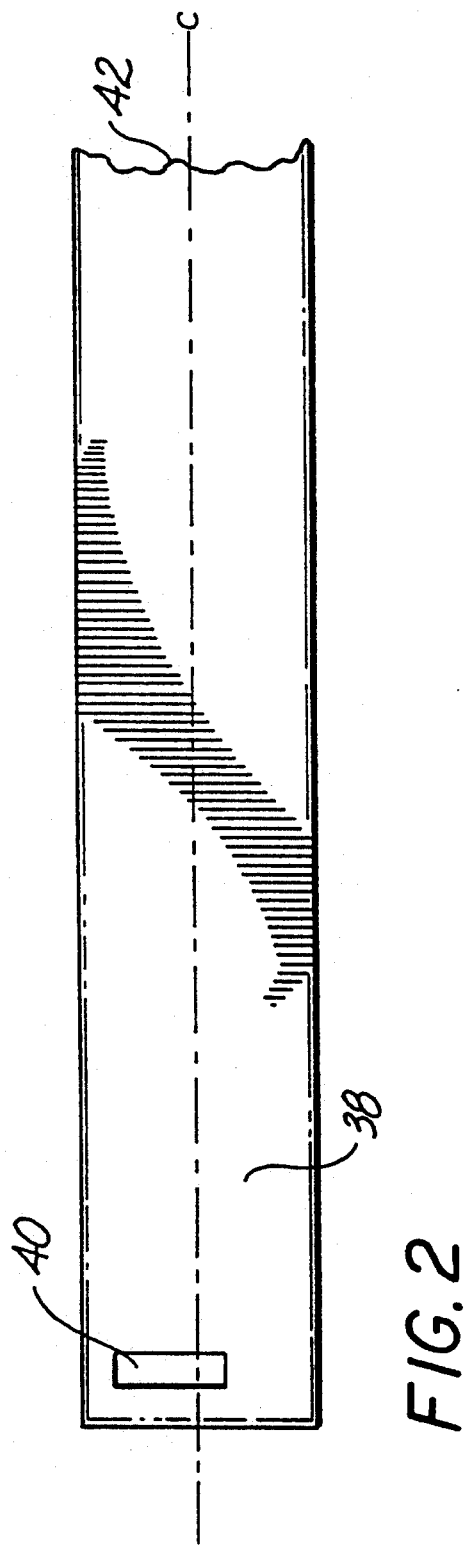
FIG. 2 is a top view of a portion of a pusher bar.

Referring to FIG. 2, an elongated pusher bar 38 is slidably received within fastener track 12. Pusher bar 38 includes a transverse slot 40 at its distal end. Transverse slot 40 is asymmetric with respect to the center line of pusher bar 38. The proximal end 42 of pusher bar 38 is adapted to cooperate with an actuating mechanism which effectuates longitudinal movement of pusher bar 38 within fastener track 12 to advance and form a fastener 44.

Figure 3:
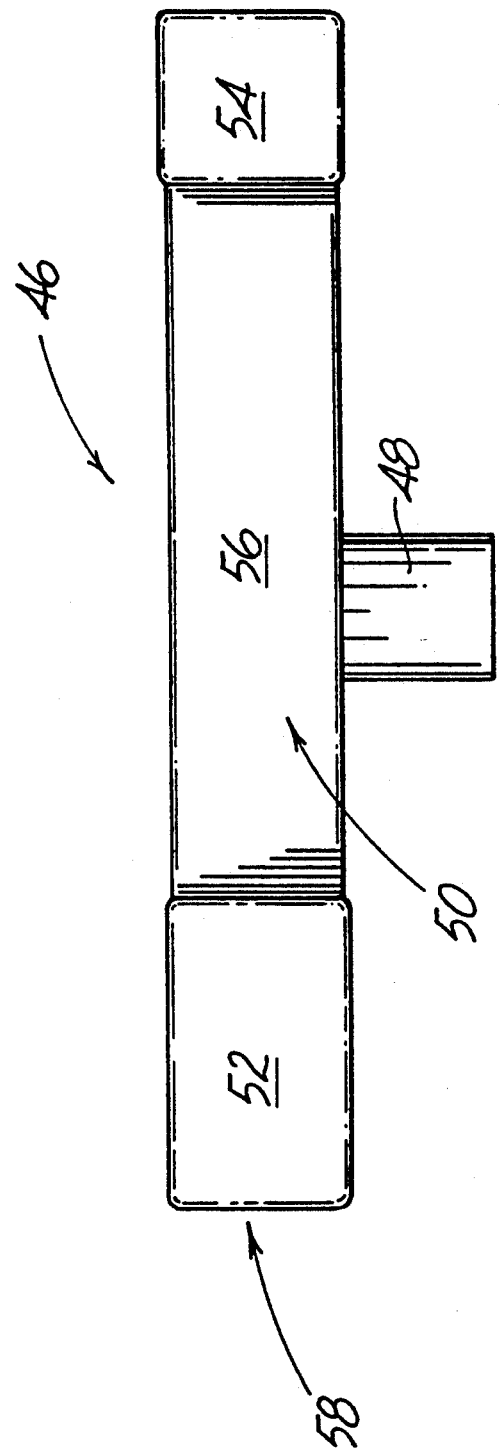
FIG. 3 is a front view of a pusher element of the invention.
Figure 4:
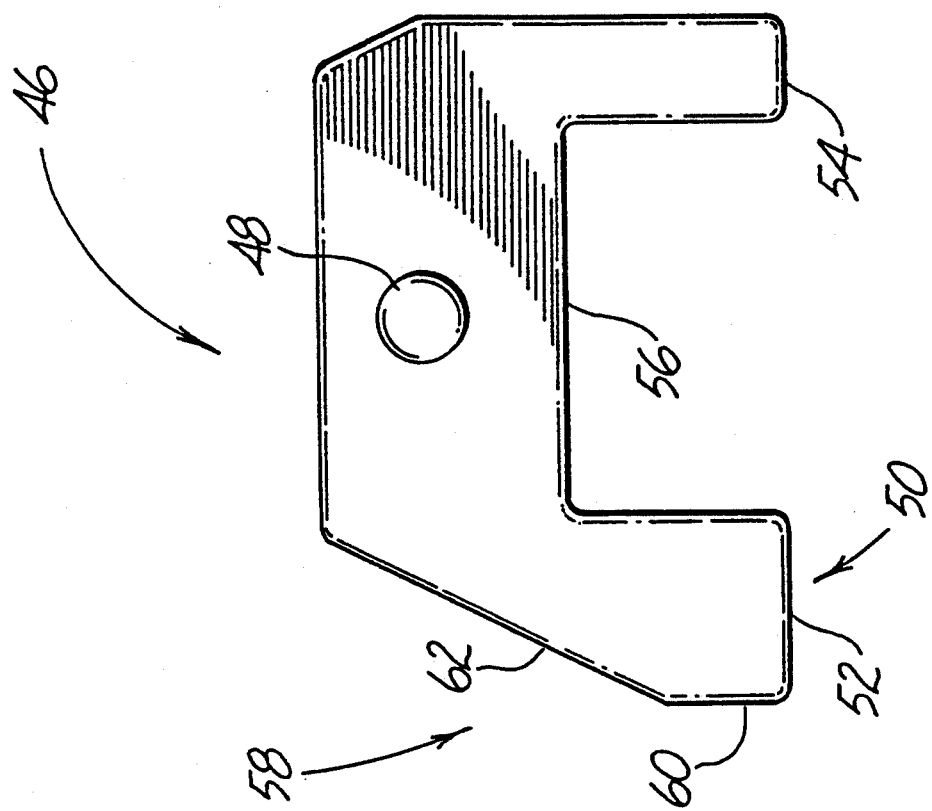
FIG. 4 is a bottom view of the pusher element.

As shown in FIGS. 3 and 4, a U-shaped pusher element 46 includes a downwardly extending pin 48. Pusher element 46 also includes a contact face 50 which includes distally pusher legs 52, 54 and a substantially U-shaped region 56. Side wall 58 includes a longitudinally directed side face 60 and angled abutment face 62. Pin 48 is sized and dimensioned to extend through and ride with transverse slot 40 in pusher bar 38, and to further extend into and ride within slot 18 in fastener track 12.

Figure 6:
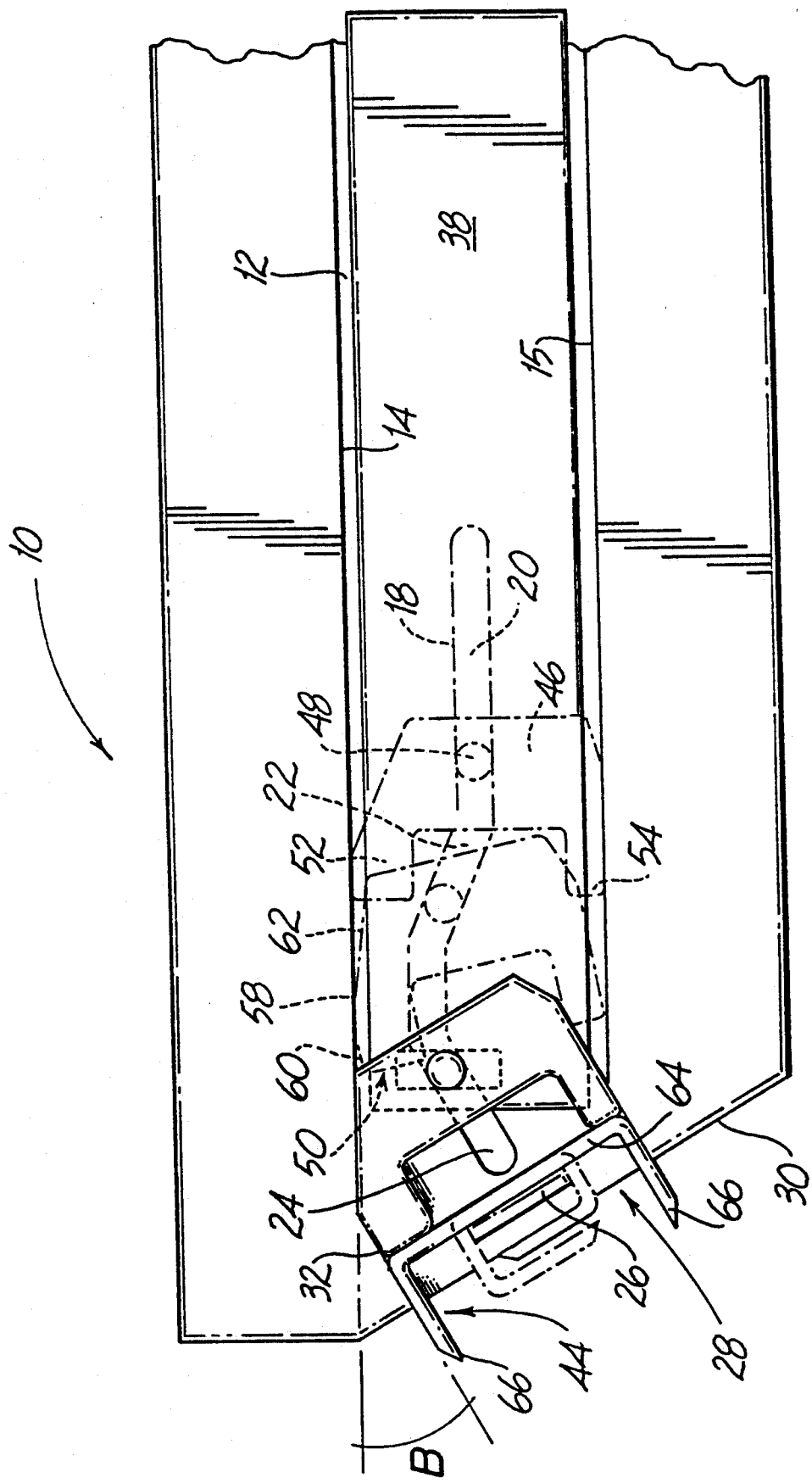
FIG. 6 is a schematic plan view of a distal portion of the fastener housing of FIG. 1 at various stages of fastener advancement.

Referring to FIG. 6., the interaction and cooperation of pusher bar 38, pusher element 46, fastener track 12, slot 18 and anvil 26 will now be described. FIG. 6 shows the above elements at various stages of fastener advance. Fastener 44 is positioned distal of and in abutment with contact face 50 of pusher element 46. In the proximal-most position of pusher element 46, pin 48 is located within first slot region 20 and within transverse slot 40 to substantially the center line of pusher bar 38.

As the pusher bar 38 is advanced distally, pin 48 enters second slot region 22 which causes pin 48 to travel within transverse slot 40 toward track wall 14. Contact between side face 60 of pusher element 46 and track wall 14 prevents transverse displacement of pusher element 46 with respect to fastener track 12 and causes counterclockwise rotation of pusher element 46 around pin 48. This counterclockwise rotation brings angled abutment face 62 into contact with track wall 14 (pusher element 46 is illustrated just prior to complete rotation). Contact face 50 of pusher element 46 thus assumes an angled orientation with respect to the longitudinal axis of fastener housing 10. Fastener 44 is brought in the same angled orientation through interaction with contact face 50. Contact face 50 and fastener 44 are preferably oriented at an Angle B to the longitudinal axis of fastener housing 10.

Figure 5:
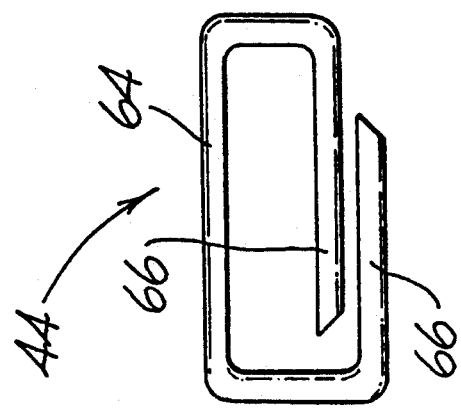
FIG. 5 is a schematic view of a preferred, formed fastener.

Further distal movement of pusher bar 38 causes pin 48 to enter third slot region 24. A pin 48 reaches third slot region 24, side wall 58 of pusher element 46 comes into contact with inwardly directed cam face 32. Pin 48 travels within transverse slot 40 toward track wall 15 as it moves distally within third slot region 24. Fastener 44 is thus advanced through the angled portion of fastener track 12. Backspan 64 of fastener 44 engages anvil 26 and pusher legs 52, 54 drive fastener 44 so as to bend fasteners legs 66 therearound (see also FIG. 5). Fastener 44 is fully formed at such time as pin 48 reaches the distal termination of slot 18.

In use, the surgeon places angled face 30 of fastener housing 10 adjacent to or against the tissue, reinforcement material or the like, to be fastened. The surgeon may, if he wishes, advance pusher bar 38 and thus fastener 44 to expose fastener legs 66 from fastener housing 10 prior to so placing fastener housing 10, to facilitate proper placement of fastener 44. Thereafter, pusher bar 38 is advanced to form fastener 44 in or around the tissue and/or reinforcement material, e.g., mesh, to be fastened.

In a preferred embodiment of the invention, fastener 44 is formed in a unique configuration which provides significant clinical advantages, particularly when used to fasten a reinforcement material to tissue, e.g., in hernia repair. The unique fastener configuration is accomplished by (i) positioning anvil 26 asymmetrically with respect to the center line of the angled portion of fastener track 12 and (ii) providing a pusher member 42 adapted to cooperate with asymmetrically positioned anvil 26 and preferably including contact legs 52, 54 of differing widths. In forming this unique fastener 44, the surgeon is able to expose greater lengths of fastener legs 66 to facilitate visualization and optimal placement because, when formed, legs 66 assume a substantially overlapping, longitudinally-spaced relation.

Referring to FIGS. 3, 4 and 6, contact leg 52 of pusher member 42 has a greater width than contact leg 54. Anvil 26 is positioned asymmetrically with respect to the center line of the angled portion of fastener track 12, being positioned more toward the side on which thinner contact leg 54 travels.

As pusher member 42 approaches anvil 26, contact legs 52, 54 pass on either side thereof. Fastener 44 is thus bent into the configuration shown in FIG. 5, with legs 66 in substantially overlapping, longitudinally-spaced relation. The arcuate travel of legs 66 as they are bent into their final configuration provides an advantageous bite into tissue and/or reinforcement material, and the overlapping, longitudinally-spaced relation provides excellent holding power. Preferably fastener legs 66, when formed, are in a substantially parallel orientation, although the exact degree to which fastener legs 66 are parallel will generally depend on the resilience of the substrate into which they are fastened.

Figures 7, 7A:
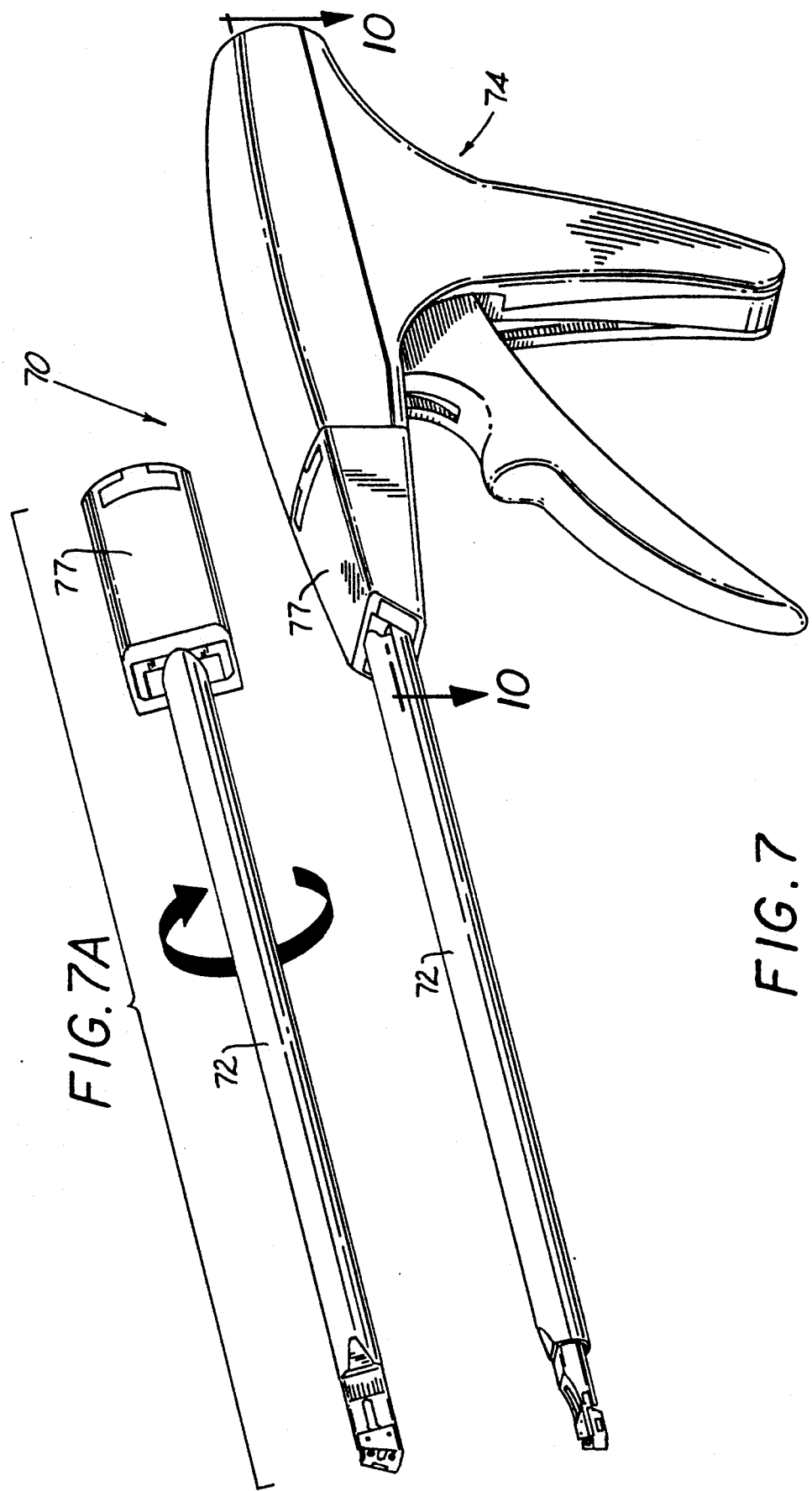
FIG. 7 is a perspective view of an endoscopic surgical instrument according to the present invention.
FIG. 7a is a perspective view of a portion of the surgical instrument shown in FIG. 7 being rotated.
Figure 10:
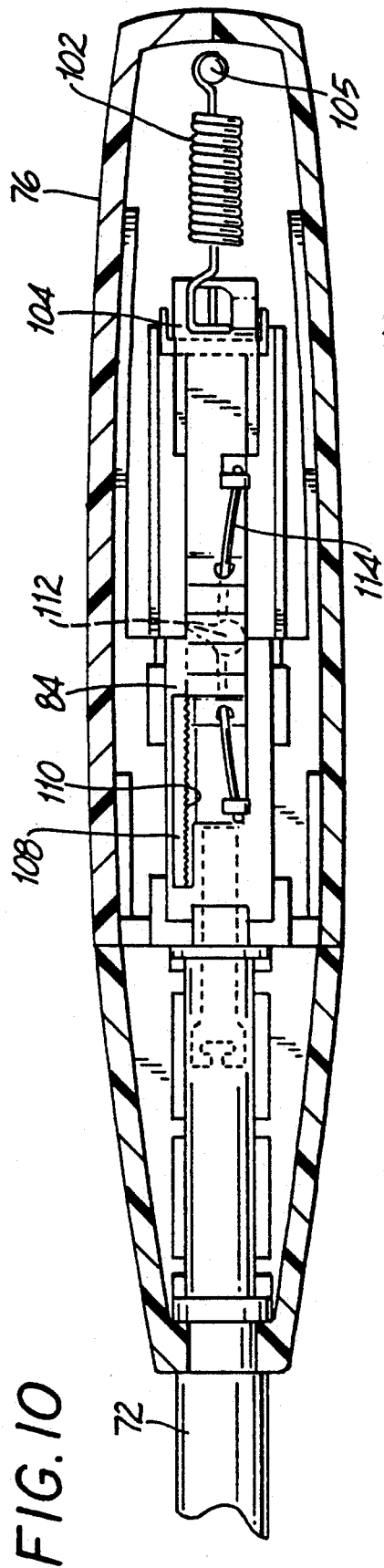
FIG. 10 is an enlarged cross-sectional view taken along lines 10—10 of FIG. 7 illustrating the mechanism at the proximal end of the instrument for providing controlled distal movement to advance and to close fasteners at the distal end.

Referring to FIGS. 7 and 7a there is illustrated a preferred embodiment of the present invention particularly adapted for endoscopic application of surgical fasteners. The fastener housing 10 is preferably incorporated at the distal end of an endoscopic surgical instrument 70. More specifically, the endoscopic surgical instrument 70 preferably includes an elongated endoscopic section 72 extending proximally from the fastener housing 10. A handle section 74 is attached at the proximal end of the elongated endoscopic section 72.

The materials utilized in the elongated endoscopic section 72 and the handle section 74 include such materials as polycarbonate for housing sections and related components, and stainless steel for such components which transmit forces. One preferred polycarbonate material is LEXAN brand polycarbonate available from General Electric Company. Other specific preferred materials such as nylon or glass filled nylon (for strength) are also utilized. However, equivalent alternative materials may be used.

It is also contemplated and within the scope of the invention to construct the endoscopic section 72 to be selectively detachable whereby the handle section 74 may be sterilized and reused, or the endoscopic section 72 can be sterilized, and the fastener housing 10 reloaded with fasteners for re-use. Alternatively, a replacement fastener magazine may be reloaded in the endoscopic section 72, and optionally a replacement endoscopic section 72 may be detachably secured to a disposable handle 74 for multiple use during a single surgical procedure. Moreover, the instrument shown may be entirely disposable. Thus, any combination of alternatives may be incorporated within the scope of the invention.

Referring to FIG. 8, there is shown a preferred handle section 74 of the instrument 70 with associated components. The handle section 74 includes an outer housing preferably formed of a polycarbonate material in separate sections as shown. The separate sections are attached, for example, by welding, adhesives, etc. One purpose of the handle section 74 is to provide controlled distal movement of the pusher means and more specifically, the pusher element 46 at the distal end of the pusher bar 38, a portion of which is shown in FIG. 6.

The handle section 74 of the endoscopic surgical instrument 70 includes a handle grip 76 and a pivotal handle trigger mechanism 78 which is pivoted toward and away from the handle grip 76. The trigger mechanism 78 is pivoted toward the handle grip 76 during the fastener advancing and firing sequence which will be described in further detail below. The handle trigger mechanism 78 pivots away from the grip 76 to return the instrument 70 to the pre-fired condition in position for firing the next fastener.

Figure 9:
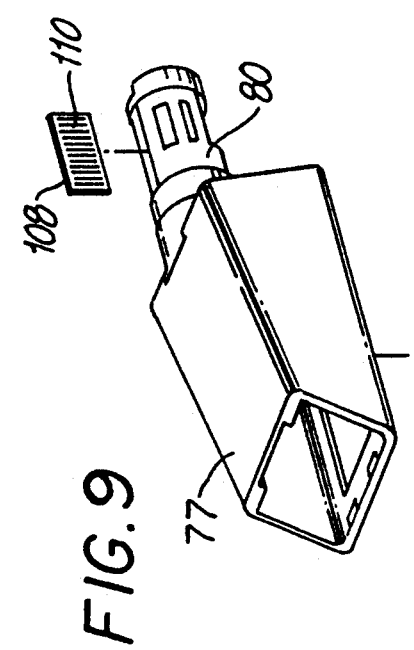
FIG. 9 is a perspective view of a rotatable nose assembly of the endoscopic surgical instrument shown in FIG. 7.

As shown in FIGS. 6 and 13, the pusher bar 38 preferably extends through the elongated endoscopic section 72. The endoscopic section 72 is rotatably attached to the handle section 74 via a rotatable nose assembly 77 having a bottom cover plate 78, shown in FIGS. 7-9. The rotatable nose assembly 77 is adapted to rotate the entire endoscopic section 72 a full 360 degrees as will be described hereinbelow. Further, a barrel portion 80 is integral with the rotatable nose assembly 77 and is configured and dimensioned for receiving a thrust bar assembly 82.

Referring back to FIG. 8 thrust bar assembly 82 includes a thrust bar 84 connected to the pusher bar 38 shown in FIG. 6. The thrust bar 84 has a ridge 86 at its distal end for mating with a hole 88 at the proximal end of the pusher bar 38 shown in FIG. 13 and more fully described below. The hole 88 is slightly larger than the ridge 86 of the thrust bar 84 to provide longitudinal movement of the ridge 86 within the hole 88. The oversized hole 88 provides a small degree of relative movement between the thrust bar assembly 82 and the pusher means. This small degree of movement provides several advantages. For example, minor proximal movements of the trigger mechanism 78 will not immediately result in engagement between the pusher means and the next available fastener, thus avoiding inadvertent distal movement of the fastener during handling by operating room personnel or positioning by the user. Also engagement of the pusher bar 38 with the next fastener will not occur until the pawl and ratchet plate of the clutch mechanism 106 (described below) takes place, thus preventing inadvertent partial advancement of several fasteners at a time. This would occur if the operator were allowed to partially activate the trigger mechanism 78 several times over the same part of its cycle. The clutch mechanism 106 prevents such movements. Further, this free movement of the thrust bar 84 permits the fastener advancing and forming components to engage each other smoothly without jamming or intercomponent interference with themselves.

A curved link 90 is pivotably connected at a lower portion to the trigger mechanism 78 by a proximal shaft 92. The trigger mechanism 78 is pivotally attached to the handle grip 76 by an upper pivot pin 94, thus providing for pivotal movement towards and away from the handle grip 76. Movement of the trigger 78 towards the grip 76 produces rotational movement of the curved link 90 because the shaft 92 traverses an upward arc whose center of rotation is located at the upper pivot pin 94.

An upright member 96 is pivotably attached towards its upper end by shaft 98 to the upper portion of the curved link 90. The upright member is also pivotably attached towards its lower end by pin 100 to the handle grip 76, as shown in FIG. 8. Since the upright member 96 is pivotably attached at upper and lower points 98, 100 respectively, the rotational motion of the curved link produces longitudinally directed distal and proximal motion of the upright member 96.

Thrust bar assembly 82 is connected to upright member 96 through an aperture 33 in the upright member 96 such that the inward squeezing of trigger mechanism 78 will cause the entire thrust bar assembly 82 to advance distally against the constant force provided by the spring 102. The spring 102 is normally biased in the coiled configuration. One end of the spring 102 is attached to a spring nub 104 at the upper end of the upright member 96, and the other end is attached to the handle grip 76 by post 105.

It can therefore be appreciated that after squeezing the trigger mechanism 78 the full stroke from the at rest position to the actuated position, release of the trigger mechanism 78 will permit the spring 102 to assume control and to return to the pre-fired original unloaded configuration. This motion in turn causes the entire thrust bar assembly 82 to return to the proximal most pre-fired position.

Referring now to FIGS. 8-12, the structure and function of the preferred uni-motion clutch mechanism 106 will be described. The clutch mechanism 106 prevents proximal movement of the thrust bar assembly not shown in FIGS. 9-12 in the event the trigger mechanism 78 is released after the squeezing motion of the trigger mechanism 78 and the advancement of the thrust bar assembly not shown in FIGS. 9-12 has begun, but before the full stroke is completed. The clutch mechanism 106 is self-releasing when the thrust bar assembly not shown in FIGS. 9-12 reaches the distal most position, thus permitting the entire thrust bar assembly not shown in FIGS. 9-12 to return to the pre-fired, or proximal most condition, and the trigger mechanism 78 to also return to the pre-fired position.

A ratchet plate 108 is fixed to the barrel 80 and includes a plurality of right angle triangular shaped parallel ridges 110. A pawl 112 is rockably mounted for distal and proximal movement with the thrust bar assembly 82 and is biased toward the ratchet plate 108 by a resilient wire spring 114 as shown. Pawl 112 is preferably formed of stainless steel while the ratchet plate 108 is preferably made of brass or other comparable material.

Figure 11:
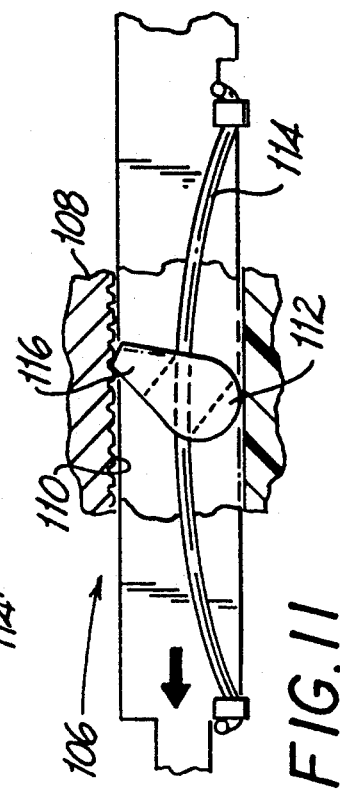
FIG. 11 is an enlarged cross-sectional view of the pawl an ratchet system in the handle section which prevents proximal movement of the fastener advancing system after distal movement has begun.
Figure 12:
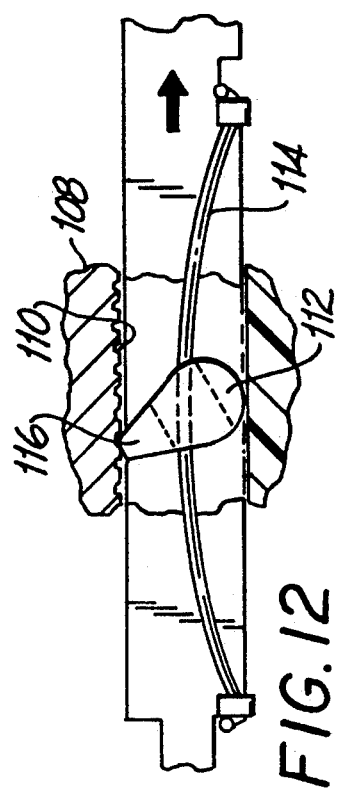
FIG. 12 is a view similar to FIG. 11 illustrating the pawl and ratchet system of FIG. 11 after a fastener has been fired and during the proximal movement of the firing mechanism.

When the trigger mechanism 78 is squeezed toward the handle grip 76 producing distal motion of the entire thrust bar assembly 82, the pawl 112 engagably slides distally past the ratchet surface 56 of the ratchet plate 52 as shown in FIG. 11 such that one corner of the tip 62 of the pawl 112 sequentially engages each right angled ridge of the ratchet plate 52 to thereby prevent proximal movement of the thrust bar assembly 82 in the event the trigger mechanism 78 is released by the operator. The engagement of the pawl 112 with the ratchet plate 108 provides audible confirmation that the pusher assembly is moving distally since the user will hear a series of audible clicks. This action continues with the tip 116 of pawl 112 sliding past the ratchet surface of the ratchet plate 108 until the pawl 112 is positioned distally of the distal most ridge.

After completion of the fastener firing stroke and upon release of the trigger mechanism 78, the pawl 112 moves proximally with the thrust bar assembly 82 under the action of the spring 102 as described above. The tip 116 of the pawl 112 which is now free, engages the distal end of the ratchet plate 108 causing the pawl 112 to rock to the reverse direction shown in FIG. 12 so as to slide proximally past the ratchet surface of the ratchet plate 108 without interference to the proximal movement of the thrust bar assembly 82.

Referring to FIGS. 8-12, when the handle grip 76 is positioned in the palm of the user's hand and the trigger mechanism 78 is squeezed toward the handle grip 76, the pin 92 of the trigger travels in a generally upward direction pushing the curved link 90 upwardly and distally in a generally counterclockwise direction. Simultaneously, the upright member 35, to which the curved link is attached via pivot point pin 98 in the upper portion of the curved link, pivots distally about the point of rotation defined by the pivot pin 100 located at the lowermost end of the handle grip 76.

The upright member's distal movement approximates the thrust bar assembly 82 distally and consequently moves the pusher bar 38 distally. As a result, the uni-motion clutch mechanism 106 is engaged as described above. The clutch mechanism 106 effectively permits squeezing the trigger mechanism 78 toward the handle grip 76 while maintaining positions midway through the stroke in the event the operator releases the grip, and permits return motion after the stroke has been completed.

The clutch mechanism 106 also allows the operator to advantageously preposition a fastener such that the legs of the fastener protrude from the distal end of the fastener housing 10 and then release pressure from the trigger mechanism 78. The operator may then turn full attention to locating the prepositioned fastener in the desired target location, at which point the pivoting of the trigger mechanism 78 may be resumed and the cycle completed. This fastener prepositioning greatly facilitates fastener placement.

Although the preferred embodiment described herein and illustrated in the accompanying drawings depicts a preferred technique, i.e. handle section 74, for actuating the pusher means, other techniques having associated mechanisms and related structure may be employed.

Referring to FIG. 13, the elongated endoscopic section 72 is shown in exploded view with parts separated for convenience of illustration. The endoscopic section 72 includes an upper housing half section 118 and a lower housing half section 120. The housing half sections are preferably of a polycarbonate material such as LEXAN brand material mentioned previously, and may be attached by welding, adhesives, etc.

The pusher bar 38 and the U-shaped pusher element 46 are positioned between the upper and lower housing half sections as described above and shown in FIG. 6. An anvil section 122, preferably formed of stainless steel, includes the anvil 26, as described above and shown in FIGS. 1 and 6, and an elongated anvil portion 124 integral with the anvil and extending proximally from the anvil 26. The elongated anvil portion includes upwardly extending feet 126 at its proximal end. The elongated anvil portion 124 further includes an elongated slot 132 towards its proximal end dimensioned and configured to slidably mate with the raised portion 134 of the pusher bar 38 (described below).

The anvil 26 is positioned within the fastener housing 10 at the distal end of the instrument 70, as shown in FIG. 6 and 13. The proximal connection points of the elongated anvil portion include upwardly extending feet 126 which are engagable within slots in the rotatable nose assembly 77 of FIG. 9. Thus, the endoscopic portion of the instrument 70 is positively connected to the handle section 74 by the upwardly extending feet 126 and is rotatable via the rotatable nose assembly 77.

The elongated anvil portion 88 stabilizes the dimension of the endoscopic section 72. The stabilizing effect prevents forces acting on the components from stretching or compressing the upper and lower housing half sections 118, 120 of the endoscopic section 72. Thus, the elongated anvil portion provides dimensional stability to the endoscopic section 72 while the endoscopic section 72 is supporting the components being subjected to forces for supporting, advancing, and forming the surgical fasteners.

The upper housing half section 118 is generally semicircular in shape and preferably includes a central groove 128 along its innerside for guiding a coiled main spring 164. Similarly, the lower housing half section 120 of the endoscopic section 72 is generally semicircular in shape and preferably includes a central groove 130 substantially identical to the groove 128 for guiding a coiled main spring 164 in concert with the groove 128 in the upper housing half section 118.

The pusher bar 38 includes a raised portion 134 at its proximal end. The raised portion includes a hole 88 configured and dimensioned for accepting the ridge 86 in the thrust bar assembly 82. The pusher element 46 is connected at the distal end of the pusher bar 38.

A pusher shroud 136 is positioned at the distal end of the pusher bar 38 and holds the pusher element 46 in place. The pusher element 46 in place at the distal end of the pusher bar 38 is preferably a pusher shroud 136. The pusher shroud 136 is connected to the bottom of the pusher bar 38, for example, by welding or rivets. As described above and shown in FIGS. 4, 6 and 13, the pusher element 46 includes a pin 48 rotatably mating with an elongated opening 138 in the pusher bar 38 and advances the fasteners in the fastener housing 10 for application.

An ejector spring 140 is located in the fastener housing 10 and includes downwardly projecting legs 141. The legs 141 are configured and dimensioned to position the fasteners advanced by the pusher element 46 in an engagable position with the anvil 26 and provide the desired force to assist in ejecting the fastener from the fastener housing after the fastener has engaged the anvil 26.

Attached to the bottom of the elongated anvil portion 124 is a guide lift spring 142 which is positioned between the elongated anvil portion 124 and the pusher bar 38. A slot 144 in the guide lift spring 142 includes an open distal end and partially overlaps the slot 18 in the fastener housing track 12. The guide lift spring 142 aligns the pusher element 46 in the fastener housing track slot 18 by encouraging the pin 48 of the pusher element 46 to communicate with the slot 144 in the guide lift spring 142. The pusher element 46 is thus guided by the open ended slot 144 while advancing a fastener.

A front fastener plate 146 is positioned within the lower housing half section 120 and beneath the pusher bar 38. The distal end of the fastener front plate 146 is configured and dimensioned to align the fasteners and assist in positioning the fasteners as they are cued forward by the fastener pusher. The front fastener plate includes at its distal end two distally extending prongs 148 and a downwardly extending flap 150. A fastener fits between the two distally extending legs 148 of the front fastener plate 146 which are preferably part of a generally U-shaped configuration formed at the distal end of the front fastener plate 146. The flap 150 communicates with the crown of the fastener and assists in maintaining the faster in a desirable position for the pusher element 46 to advance the fastener in the fastener housing 10.

Working in concert, the front fastener plate 146 and the lower housing half section 120 position the fasteners therebetween maintaining alignment of the fasteners as they are advanced by the fastener pusher 156. Moreover, when the fastener pusher 156 approaches its distal most position, the downwardly extending flap 150 of the front fastener plate 146 communicates with the top of the fastener pusher 156 to assist in stabilizing the pusher 156 such that the fasteners continue in the appropriate path.

A rear fastener plate 152 communicates with the proximal end of the front fastener plate 146 and extends proximally with respect to the front fastener plate 146. The rear fastener plate 152 includes an elongated hole 154 which is configured and dimensioned to receive a upwardly extending tab 160 at the proximal end of a fastener pusher 156.

The fastener pusher 156 is slidably positioned between the rear fastener plate 152 and the lower housing half section 120. The fastener pusher 156 includes a pusher head 158 at its distal end having a generally U-shaped tip and an upwardly extending tab 160 at its proximal end. The pusher head 158 is dimensioned and configured to communicate with the crown and legs of a fastener, thus providing positive interaction between the fastener and the fastener pusher 156.

An upwardly extending tab 160 is located at the proximal end of the fastener pusher 156, and a spring guide 162 is attached to the bottom of the fastener pusher 156 via conventional means, and extends generally downward. The fastener pusher 156 is biased in the distal direction by a coiled main spring 164 communicating with the tab 160 and the spring guide 162. Thus, a fastener or a plurality of fasteners may be biased in the distal direction such that the fasteners may be sequentially fired.

The coiled main spring 164 is positioned within the groove 130 in the lower housing half section 120 and extends upwardly in a coiled fashion through the elongated hole 154, the elongated opening 138, and the elongated slot 132 to communicate with the groove 128 in the upper housing half section 118. Thus, the coiled main spring 164 is guided by the grooves 130, 128 in the upper and lower housing half sections 120, 118. Spring 164 biases the fastener pusher 156 distally by communicating with the proximal side of the tab 160 and the spring guide 162.

A fastener feed plate 166 is positioned at the distal end of the lower housing half section 120 and includes two parallel distally extending feet 168. A portion of the feet 168 are inclined upwardly to advance a fastener to a desired elevated position. More specifically, the feet 168 are configured and dimensioned such that as a fastener is moving over the fastener feed plate 166 in the distal direction the fastener is elevated upwardly as it advances over the feet 168.

A gas sealing means 170 includes a substantially circular body having an aperture therethrough. The gas sealing means 170 is positioned distally to the rotatable nose assembly 77 and between the upper and lower housing half sections 118, 120. The gas sealing means 170 effects a substantial internal seal within the endoscopic section 72 of the instrument 70. The gas sealing means 170 is configured and dimensioned to accommodate longitudinal movement of the pusher bar 38 and the fastener pusher 156 while discouraging gasses used to insufflate the body cavity from egressing through the endoscopic section 72. Although the gas sealing means 170 is designed as described above and as shown in the accompanying drawings, it is contemplated that other gas sealing means having different configurations may be used.

It is also contemplated that the fastener feed plate 166 described above and illustrated in the accompanying drawings may be configured and dimensioned differently, while providing the specified elevation of the fastener in a similar fashion to fastener feed plate 166.

A lubricant may be used on or about any of the internal parts discussed above in the handle section 74 or the endoscopic section 72 of the instrument, such as between a moving part and a non-moving part, or between two moving parts. Lubricant may be used, for example, between the lower housing half section 120 and the pusher bar 38 and/or the fastener pusher 156. The lubricant is used for reducing frictional resistance and providing smooth interaction between the parts. A desirable lubricant may be, for example, a lithium grease, or a silicone grease.

In operation, after the endoscopic section 72 enters the body cavity insufflated with gas, the sealing means 170 impedes deflation of the body cavity by discouraging gasses from escaping past the endoscopic section 72. Next, as the handle trigger mechanism 78 is pulled towards the handle grip 76, the pusher bar 38 is actuated distally by the interaction between the thrust bar 84 connected to the pusher bar 38 by ridge 86. The pusher element 46 attached to the pusher bar 38 via pin 48 advances a fastener already in position in the fastener housing 10. The fastener is applied by engagement with the anvil 26 as described above.

After a fastener is applied, a vacancy in the fastener housing 10 is filled by another fastener biased to move distally by the coiled main spring 164 positioned proximal the fastener pusher 156. A fastener is moved to assume the ready position in the fastener housing 10 by the fastener pusher 156 advancing the fastener with the pusher head 158. A plurality of fasteners may be positioned proximal the fastener pusher 156 and can be biased in the distal direction by interaction with the pusher head 158 of the fastener pusher 156.

The fastener is moved upwardly from communicating with the fastener pusher 156 to being positioned for engagement with the anvil 26 via the fastener feed plate 166. As the fastener progresses over the fastener feed plate 166 in the distal direction, the fastener is elevated upwardly as it advances over the feet 168. The front fastener plate 146 assists in positioning the fastener for distal movement for advancement by the pusher element 46 by accommodating the fastener with its generally U-shaped distal end. As the fastener pusher 156 approaches its distal-most position, the downwardly extending flap 150 of the front fastener plate 146 communicates with the top of the fastener pusher 156, thereby stabilizing the pusher 156 such that the fasteners continue in their appropriate path. Thus, the interaction of the fastener pusher 156, the front fastener plate 146, and the pusher element 46 enable sequential application of fasteners.

Although the pusher head and the distal end of the front fastener plate have generally U-shaped configurations in the preferred embodiment described herein and shown in the accompanying drawings, other shapes may be desirable.

Further, other means having related structure to that shown in the preferred embodiment described herein and illustrated in the accompanying drawing may be used to advance fasteners sequentially.

While the above description contains many specifics, these specifics should not be construed as limitations on the scope of the invention, but nearly as exemplifications of preferred embodiments thereof. Those skilled in the art will envision many other possible variations that are within the scope and spirit of the invention as defined by the claims appended hereto.

What is claimed is:

1. A surgical instrument for placing a fastener in or on tissue comprising:
    (a) a fastener housing having anvil means mounted at one end thereof and adapted to house at least one fastener therein;
    (b) pusher means slidably received by said fastener housing, said pusher means comprising a pusher bar which defines a longitudinal axis and a pusher element slidably mounted to said pusher bar;
    (c) slot means in said fastener housing, wherein said pusher means cooperates with said slot means to angularly displace said pusher element with respect to said longitudinal axis as said pusher means is advanced through said fastener housing; and
    d) means for actuating said pusher means being positionable proximal of said fastener housing.

2. The surgical instrument of claim 1, wherein said means for actuating further comprises:
    an elongated endoscopic section extending proximally from said fastener housing and substantially encasing said pusher means; and
    a handle section couplable with said elongated endoscopic means at an opposite end from said fastener housing, said handle section cooperating with said pusher means to manually and selectively activate said pusher means.

3. The surgical instrument of claim 2 wherein said elongated endoscopic section includes a rotatable portion positioned distally from said handle section.

4. The surgical instrument of claim 2 wherein said elongated endoscopic section is configured and adapted for insertion into endoscopic tubular means.

5. The surgical instrument of claim 2, further comprising means for preventing proximal movement of said pusher means after said pusher means has moved distally a predetermined amount.

6. The surgical instrument of claim 2 further comprising gas sealing means to prevent gases from egressing through the endoscopic portion.

7. A fastener-forming assembly comprising:
    (a) a fastener housing defining a fastener track having a center line and an opening at one end adapted to permit fastener exit, said fastener housing further including pusher means disposed therein;

(b) anvil means positioned adjacent said opening, said anvil means being positioned in a transverse and non-symmetrical orientation with respect to said center line;

(c) a fastener having a backspan and a pair of legs extending from the backspan at either end thereof; wherein contact of said fastener with said non-symmetrically positioned anvil causes said backspan of said fastener to bend such that said fastener legs assume a substantially over-lapping, longitudinally-spaced relation; and (d) means for actuating said pusher means, said means for actuating being positionable proximal of said fastener housing.

8. The surgical instrument of claim 7, wherein said means for actuating further comprises:

an elongated endoscopic section extending proximally from said fastener housing and substantially encasing said pusher means; and a handle section couplable with said elongated endoscopic means at an opposite end from said fastener housing, said handle section cooperating with said pusher means to manually and selectively activate said pusher means.

9. The surgical instrument of claim 8 wherein said elongated endoscopic section includes a rotatable portion positioned distally from said handle section.

10. The surgical instrument of claim 8 wherein said elongated endoscopic section is configured and adapted for insertion into endoscopic tubular means.

11. The surgical instrument of claim 8, further comprising means for preventing proximal movement of said pusher means after said pusher means has moved distally a predetermined amount.

12. The surgical instrument of claim 8 further comprising gas sealing means to prevent gases from egressing through the endoscopic portion.

* * * * *